(12) United States Patent
Forsell

(10) Patent No.: US 9,028,546 B2
(45) Date of Patent: May 12, 2015

(54) ARTIFICIAL VALVE FOR IMPLANTATION

(76) Inventor: Peter Forsell, Bouveret (CH)

( * ) Notice: Subject to any disclaimer, the term of this patent is extended or adjusted under 35 U.S.C. 154(b) by 100 days.

(21) Appl. No.: 13/384,376

(22) PCT Filed: Jul. 13, 2010

(86) PCT No.: PCT/EP2010/060080
§ 371 (c)(1),
(2), (4) Date: Jan. 17, 2012

(87) PCT Pub. No.: WO2011/006902
PCT Pub. Date: Jan. 20, 2011

(65) Prior Publication Data
US 2012/0116497 A1   May 10, 2012

Related U.S. Application Data

(60) Provisional application No. 61/213,820, filed on Jul. 17, 2009.

(51) Int. Cl.
*A61F 2/24* (2006.01)

(52) U.S. Cl.
CPC ....... *A61F 2/2421* (2013.01); *A61F 2250/0001* (2013.01)

(58) Field of Classification Search
USPC .......... 623/1.26, 2.1–2.41, 3.1–3.3; 251/129.11, 129.12, 129.13, 129.15, 251/129.16, 142, 149, 2, 149.5, 149.9, 286; 137/615–616.7, 625.31
See application file for complete search history.

(56) References Cited

U.S. PATENT DOCUMENTS

| | | | |
|---|---|---|---|
| 1,194,358 A | 8/1916 | Cecil et al. |
| 3,771,173 A | 11/1973 | Lamb |
| 4,304,261 A | 12/1981 | Forester |
| 4,599,081 A | 7/1986 | Cohen |
| 4,623,350 A | 11/1986 | Chareire |
| 4,674,537 A | 6/1987 | Bergmann |
| 5,181,580 A | 1/1993 | Burg |
| 5,326,374 A | 7/1994 | Ilbawi et al. |
| 5,342,026 A | 8/1994 | Hwang |
| 6,979,351 B2 | 12/2005 | Forsell |

(Continued)

FOREIGN PATENT DOCUMENTS

| | | |
|---|---|---|
| EP | 0102548 A2 | 3/1984 |
| EP | 0412191 A1 | 2/1991 |

(Continued)

OTHER PUBLICATIONS

International Search Report for PCT/EP2010/060080, mailed Sep. 27, 2010.

(Continued)

*Primary Examiner* — David Isabella
*Assistant Examiner* — Suba Ganesan

(57) ABSTRACT

An artificial heart valve consists of two or more valve members (10, 20) stacked one upon the other in a housing (40) and having blood flow passages (13, 23) that can be aligned with each other in order to open the valve and allow blood flow through the valve and that can be disaligned to close the valve. The valve members are maintained in continuous rotation and the alignment and disalignment of the valve members is achieved by slowing down and reaccelerating one or more of the valve members using a drive (18, 28) appropriately controlled by a control unit (C).

25 Claims, 11 Drawing Sheets

(56) References Cited

U.S. PATENT DOCUMENTS

| | | |
|---|---|---|
| 7,238,165 B2 | 7/2007 | Murphy |
| 2002/0072698 A1 | 6/2002 | Tung |
| 2003/0069547 A1 | 4/2003 | Gonon |
| 2004/0024285 A1 | 2/2004 | Muckter |
| 2004/0068299 A1 | 4/2004 | Sigg |
| 2004/0098113 A1 | 5/2004 | Forsell |
| 2005/0060030 A1 | 3/2005 | Von Hoffmann |
| 2005/0222678 A1 | 10/2005 | Kusleika |
| 2006/0025855 A1 | 2/2006 | Bishop |
| 2006/0074484 A1 | 4/2006 | Huber |
| 2006/0178552 A1 | 8/2006 | Gross |
| 2007/0204924 A1 | 9/2007 | Delgiacco |
| 2007/0225802 A1* | 9/2007 | Forsell ............ 623/2.34 |
| 2007/0246678 A1* | 10/2007 | Michaels ............ 251/304 |
| 2007/0276480 A1 | 11/2007 | Cook |

FOREIGN PATENT DOCUMENTS

| | | |
|---|---|---|
| EP | 1514526 A2 | 3/2005 |
| GB | 1 194 358 | 6/1970 |
| WO | WO 2007/051568 | 5/2007 |

OTHER PUBLICATIONS

Written Opinion for PCT/EP2010/060080, mailed Sep. 27, 2010.

* cited by examiner

ARTIFICIAL VALVE FOR IMPLANTATION

This application is the U.S. national phase of International Application No. PCT/EP2010/060080, filed 13 Jul. 2010, which designated the U.S. and claims the benefit of U.S. Provisional No. : 61/213,820, files 17 Jul. 2009, the entire contents of each of which are hereby incorporated by reference.

BACKGROUND OF THE INVENTION

The present invention relates to an artificial valve for implantation in a patient's blood vessel, in particular an artificial heart valve, and specifically relates to an artificial valve system including such an artificial valve.

Artificial heart valves are generally designed to replace the natural heart valve and to perform its function over many years, preferably until the person (or animal) dies. Thus, besides the general requirement that artificial valves must be made from a material that is compatible with the patient's blood and tissue, the valve must furthermore be extremely reliable.

Typical artificial heart valves are strictly mechanical, such as mechanical mono- or bi-leaflet valves and ball valves. A leaflet valve may for instance comprise a tilting disc hinged to an annular ring that is sutured into the blood vessel. The blood pressure changes of typically between 80 mmHg and 120 mmHg cause the disc to swing between an open and a closed position. In ball valves, a ball is held in a cage and allowed to move therein upon blood pressure changes between a closed position in which it seals an annular ring sutured into the blood vessel and an open position in which the ball is at a distance from the ring, thereby permitting blood to flow around the ball.

While there are many different types of artificial valves for implantation in a patient's blood vessel, they all suffer from the draw back of material fatigue resulting in breakage of parts thereof. Disfunctioning of the valve is only one severe consequence thereof. The consequences may be fatal when broken parts are carried away with the blood stream and block the blood stream at remote locations. Another problem arising with artificial valves implanted in blood vessels is the danger of generating thromboses as well as fibrosis forming and growing on the valve elements. Particularly the latter may prevent complete closing of the valve, thereby causing valve insufficiency.

There has been suggested in WO 2007/051568 an artificial valve for implantation in a patient's blood vessel, in particular an artificial heart valve, which is mechanically reliable over a long period of time without its closing efficiency being substantially affected by fibrosis. It is further described therein an entire valve system comprising such an artificial valve and further components. The present invention is an improvement to the valve and valve system described in WO 2007/051568 and, therefore, the function of the known valve will now be described in detail insofar as it applies also to the present invention.

More specifically, the artificial valve known from WO 2007/051568 comprises a first and a second valve member, each having a first smooth surface. The first smooth surfaces of the first and second valve members face each other so as to form a sealing contact between the first and second valve members. The first and second valve members further each have at least one blood flow passage extending from the first smooth surface to a second surface located on an opposite side of the respective valve member, wherein the first valve member is arranged so as to be slidably displaceable relative to the fixedly mounted second valve member such that the passage of the first valve member can be brought into at least partial alignment with the passage of the second valve member while maintaining the sealing contact between the first and second valve members. The artificial valve further comprises a displacing mechanism for the relative displacement of the valve members so as to bring their blood flow passages into and out of said at least partial alignment.

This way, blood flow through the valve can be controlled by sliding displacement of the valve members relative to one another, thereby aligning and disaligning the blood flow passages, i.e. opening and closing the valve. The smooth surfaces forming the sealing contact and the fact that opening and closing of the valve is performed by sliding displacement of the smooth surfaces relative to each other prevent any fibrosis formation on the sealing surfaces. Thus, the sealing efficiency will not deteriorate over time. Furthermore, due to the valve members being displaced relative to one another in a sliding fashion, the forces acting on the valve members are relatively small, thereby overall reducing problems of fatigue of the valve member material.

In a preferred embodiment described in WO 2007/051568, the displaceable arrangement of the valve members relative to one another is such that the first valve member is rotatable relative to the fixedly mounted second valve member. This allows for the at least partial alignment and disalignment of their blood flow passages either by moving the first valve member back and forth in opposite directions of rotation or by continuously moving it in a single direction of rotation.

FIGS. 14 and 15 show the principle structure of such an artificial valve. The absolute and relative dimensions are not true to scale and the shape of the valve members may be chosen differently. The artificial valve 100 shown in FIGS. 14 and 15 comprises a first valve member 10 and a second valve member 20, composed of two halves 20a, 20b. The second valve member 20, here, forms a housing for the first valve member 10. The first valve member 10 is disc-shaped and arranged within the second valve member 20 for rotation about an axis 101, while the second valve member 20 is stationary. The first valve member 10 has a blood flow passage 13 extending from a first surface 11 to a second surface 12, and the second valve member has a blood flow passage 23a, 23b extending from a first inner surface 21 to a second outer surface 22. Upon rotation of the first valve member 10 about the axis 101, the blood flow passage 13 of the first valve member 10 may be brought into complete alignment with the blood flow passage 23a, 23b of the second valve member 20, thereby establishing flow communication through the valve 100 from an upstream side 105 to a downstream side 106 thereof. Centrally arranged within the artificial valve 100 is a displacing mechanism in the form of a motor M for displacement of the first valve member 10 relative to the second valve member 20 for turning the first valve member 10 either back and forth or always in the same direction. The displacing mechanism is contained in a cavity 102 which is formed and sealed against blood ingression by the valve members 10, 20. FIG. 15 shows the top view of the artificial valve 100 of FIG. 14, the blood flow passages 13, 23 each extending over 180° in an angular direction, more particularly somewhat less than 180° so as to prevent any flow communication between the blood flow passages 13, 23 when the valve 100 is in its closed position. The rotatably arranged first valve member 10 has to be turned by 180° to open and close the valve. Also, blood flow will be concentrated at one side of the valve 100.

It is preferred to divide the passages into a plurality of angularly extending sections which can be equally distributed about the axis of rotation. As a result, the blood flow through the artificial valve is distributed more evenly over the valve's cross section. As a further great advantage, the relative displacement of the valve members for bringing their blood flow passages into alignment is less. This can be easily appreciated for a valve having two valve members as shown in FIG. 14 and having passages with an overall angular extension of 180° (or somewhat less), however, the passages being subdivided into e.g. four sections of 45° equally spaced apart about the common axis, as shown in FIG. 16. Instead of turning the valve member by 180° to bring the blood flow passages of the two valve members into alignment (as in the case of FIG. 15), it is sufficient to turn the valve members by only 45°.

The theoretical maximum flow capacity of an artificial valve with only two valve members amounts to only about 50% of a fully opened natural valve for the simple reason that each of the two valve members must have a closed area sufficiently large to cover and close the flow passage of the respective other valve member when the valve is in its closed position. Therefore, a preferred valve comprises three of said valve members or, more preferably, even more than three valve members, arranged in series. Providing more than two valve members allows for enlarging the flow capacity of the artificial valve. For instance, in the case of three valve members, only 33% of the cross sectional area of each valve member must be closed, i.e. fluid tight, so that by appropriate arrangement of the valve members relative to each other the entire cross sectional area of the artificial valve may be closed.

However, where the artificial valve includes more than two valve members, e.g. three valve members (two displaceable and one stationary valve member) each having a blood flow passage with an angular extension of 240°, the blood flow passages of each pair of adjacent valve members overlap by 120°. As a result, backflow in a plane substantially perpendicular to the axis of rotation will occur in the valve's closed position even though, when viewed in a direction along the axis of rotation, the valve members completely cover the entire cross section of the valve. To prevent such backflow, the blood flow passages of the valve members may be divided into sections by means of more or less radially extending bridges. This is shown in FIG. 17 representing a top view of an artificial valve 100 with three valve members arranged in series. The blood flow passages 23 of each of the valve members extend over about 240°, however, the blood flow passage 23 is subdivided by a radially extending bridge 24 so as to divide the blood flow passage 23 into two sections of equal size. The bridges 24 are located at positions so as to prevent in the valve's closed position any backflow from the passage 23 of one valve member through the passage 23 of the next adjacent valve member to the passage 23 of the next over adjacent valve member. In the shown situation of three valve members, it is sufficient to have such a bridge 24 at least in the passage 23 of the centrally arranged valve member so as to separate the passage of the upper valve member from the passage of the lower valve member.

Of course, the number of bridges can be larger, and this is even preferred in order to divide the passages into a plurality of angularly extending sections which can be equally distributed about the axis of rotation. As a result, the blood flow through the artificial valve is distributed more evenly over the valve's cross section and, more importantly, the relative displacement of the valve members for bringing their blood flow passages into alignment is less. A principal example of this most complex but most efficient artificial valve with three valve members is shown as a top view in FIG. 18. In this case, the blood flow passage 23 is divided to form two sections of about 120° equally spaced apart by relatively wide bridges, and such sections are further subdivided by bridges 24 so as to form subsections of equal size. Again, the bridges 24 are needed to prevent any backflow which would otherwise occur between adjacent valve members.

One problem arising with the afore-described system is the backflow that occurs through the valve back to the heart chamber at the time when the diastolic pressure in the heart chamber reaches a minimum. This is particularly dangerous for patient's suffering from coronar blood supply problems since the coronar arteries branching off of the aorta right behind the aortic valve require high blood pressure. Those people typically have low blood pressure and little heart pump capacity. It is therefore important that the valve closes quickly. However, the problem of back flow is likewise critical in cases where the valve is provided to replace a valve within the heart, such as the tricuspidalis valve between the right ventricle and the right atrium.

SUMMARY OF THE INVENTION

It is therefore an object of the present invention to further improve the efficiency of the artificial valve and the corresponding valve system, in particular to reduce any backflow towards the heart chamber when implanted as a heart valve, such as the aortic valve or tricuspidalis valve.

This object is solved by an artificial valve and corresponding valve system of the afore-mentioned kind, however, with at least one drive for continuously rotating both the first and the second valve members. A displacing mechanism is provided for the relative displacement of the valve members and is adapted to temporarily change the relative rotational speed of the first and second valve members so as to bring into and out of at least partial alignment the at least one blood flow passage of the first valve member with the at least one blood flow passage of the second valve member. Thus, the valve members always rotate with the same rotational speed, unless when their relative position is to be changed, in which case their relative rotational speed is temporarily changed so as to open and close the blood flow passages.

By constantly rotating the first and second valve members, frictional forces during the process of bringing the blood flow passages into and out of engagement are reduced. That is, the frictional forces between the valve member and the housing in which it is slidably held, which are to be overcome when one valve member is accelerated from its stationary position in which the blood flow passages are in alignment (open) into another position in which they are out of alignment (closed), are larger as compared to the frictional forces to be overcome when the acceleration is performed in a state where the respective valve member rotates. Due to the reduced frictional forces, opening and closing of the valve members can be faster. Thus, more blood can be pumped through the valve and the back flow can be reduced, so that altogether more blood is available for the coronar arteries if the valve replaces the aortic valve.

As a further advantage, the danger of thrombosis is substantially reduced by the constant rotation of the valve members. The constant rotation causes the blood close to the valve surface to continuously move and, thereby, reduces the danger of blood coagulation in dead zones.

The relative rotational speed of the valve members for bringing their blood flow passages into and out of alignment can be achieved either by first decelerating one of the valve members and then accelerating said valve member again to the regular rotational speed, or by first accelerating one of the valve members and then decelerating said valve member again to the regular rotational speed. Of course, once a valve member has been decelerated to a slower rotational speed, it has to be accelerated again so that, at the time when alignment of the blood flow passages has been achieved, it will continue to rotate further along with the other valve member or members with the regular speed. It is particularly preferred to first decelerate and then accelerate the valve member at the time of closing the blood flow passages and first accelerate and then decelerate the valve member to open the blood flow passages again, because decelerating can be achieved easily and very quickly by slowing down the valve member such as by braking, in particular by mechanical braking action. This way, back flow through the blood flow passages can be kept little at the time when the diastolic pressure reaches its minimum.

In order to further reduce the time period of bringing the blood flow passages out of alignment ("closing"), it is advantageous not only to decelerate the one valve member but also to accelerate the respective other one of the valve members at the same time. Of course, just like the decelerated valve member has to be reaccelerated to the regular speed, the respective other one of the valve members, after having been accelerated, has to be decelerated again to the regular speed once the blood flow passages have reached their disaligned positions.

Bringing the blood flow passages into alignment again ("opening") can be achieved basically in the same manner, i.e. by first decelerating one of the valve members and then, once the aligned position has been reached, accelerating the same valve member again to the regular speed. It can be preferable to decelerate and accelerate always the same valve member both at the time of bringing the blood flow passages out of alignment and again into alignment. In this case, means for decelerating and accelerating can be limited to one or a few valve members.

However, as with the process of disaligning (closing) the blood flow passages, it can be advantageous to accelerate (and subsequently decelerate again) the respective other one of the valve members in order to speed up the aligning process (opening), although speed is not so critical in the aligning process as compared to the disaligning process for the reasons explained earlier.

Also in the case where disalignment is achieved by decelerating and re-accelerating one valve member and re-alignment is achieved by decelerating and re-accelerating the respective other valve member, it is advantageous at the time of re-alignment to accelerate (and subsequently decelerate) also the particular one valve member, in order to speed up the alignment process.

The artificial valve system may have more than only two continuously rotating valve members, e.g. three or four or even more continuously rotating valve members arranged in series. Providing more than two valve members allows for increasing the blood flow passages and, thus, enlarging the flow capacity of the artificial valve as explained earlier in relation to the prior art artificial valve. Accordingly, the drive of the artificial valve is adapted for continuously rotating also the third and further valve members. Furthermore, the displacing mechanism is adapted to temporarily change the rotational speed of the third valve member relative to the rotational speed of the first and second valve members so as to bring into and out of at least partial alignment the at least one blood flow passage of the third valve member with the blood flow passages of the first and second valve members.

For instance, where the valve has three rotating valve members, a central one of the valve members may rotate with constant speed, whereas the one valve member located on one side of the central valve member is accelerated and the other one of the valve members located on the other side of the central valve member is decelerated to bring the three valve members out of alignment, or as the case may be, into alignment.

Alternatively, an outermost of the three valve members may rotate with constant speed and the other two valve members are each decelerated appropriately so as to bring the blood flow passages of the three valve members out of alignment or, as the case may be, into alignment. It is preferable in this situation to begin the deceleration of these two valve members at the same moment to achieve disalignment or, as the case may be, alignment of the blood flow passages as quickly as possible.

While the rotational speed of two of the three valve members is temporarily changed, the respective third valve member is substantially maintained at a constant rotational speed.

In order to ensure that the valve member, the rotational speed of which is influenced, e.g. by deceleration, exactly assumes an aligned/disaligned position with respect to the other valve member or valve members and to continue to rotate with the other valve member or members in that configuration, a stopper may be provided and arranged to hold the valve members in a stable position relative to each other. For instance, when one valve member has been decelerated to achieve blood flow passage disalignment and/or has been accelerated to achieve blood flow passage alignment, this can be easily achieved with a stopper that is formed as an axial projection on one of the rotatably displaceable valve members and engages with a recess in another one of the rotatably displaceable valve members. The respective ends of the recess within which the stopper is moved upon acceleration and deceleration of the one valve member relative to the other valve member defines the end positions for the stopper, said end positions being identical with an aligned and a disaligned configuration of the valve members.

Preferably, the artificial valve is normally open so that blood can flow through the valve in the case of a failure of the displacing mechanism. Accordingly, means are provided to urge the blood flow passages into at least partial alignment when the displacing mechanism is not activated. Such means may comprise a return spring arranged for relative movement of the valve members so as to bring the blood flow passages into at least partial alignment. However, other means can likewise be used, such as magnetic forces that have to be overcome when the blood flow passages are to be brought out of alignment. Most preferably, the means for urging the blood flow passages into at least partial alignment, in particular the aforementioned return spring, acts on the stopper described before. Thus, the return spring urges the stopper against a rest which defines the aligned configuration of the valve members.

There are several possibilities to achieve relative displacement of the valve members. According to a first embodiment, the activity of the drive for continuously rotating the valve members is influenced. For instance, a separate drive may be provided for each of the rotatably displaceable valve members. The separate drives are controlled by means of a control unit so as to bring the blood flow passages of the valve members into and out of at least partial alignment. Without intervention by the control unit, the valve members are driven at the same constant speed. Using the control, the drive activity of one of the separate drives can be controlled so as to temporarily slow down one of the valve members in order to bring their blood flow passages out of alignment (or into alignment, as the case may be). This configuration will be maintained for the time of temporarily controlling the drive activity of the one separate drive. By means of e.g. the stopper described above, the valve members may be coupled to each other such that the disaligned valve member configuration is maintained for the time that the drive activity of the one separate drive is slowed down. As a side effect, the regular rotational speed of the set of valve members will slightly decrease.

Once the drive activity of the one separate drive returns to normal, the set of valve members will return to their normal regular rotational speed. Re-alignment of the blood flow passages can then be achieved e.g. by means of the return spring described before. However, where a return spring is not provided or is not strong enough (which would usually be the case) to achieve a quick re-alignment of the blood flow passages, the drive activity of the one separate drive is controlled so as to re-accelerate the previously decelerated valve member in order to bring the blood flow passages into alignment again.

According to a second embodiment, instead of providing separate drives for the valve members and controlling their drive activity, relative displacement of the valve members is achieved by means of an additional drive. The additional drive is provided for temporarily changing the relative rotational speed of at least two of the rotatably displaceable valve members and, again, a control is further provided for controlling the additional drive so as to bring the blood flow passages of the valve members into and out of at least partial alignment.

For instance, the additional drive may mechanically interconnect the valve members. It may comprise a stepper motor which has preferably two steps, one step defining the aligned configuration and the other step defining the disaligned configuration of the valve members. The stepper motor may be a reciprocating stepper motor or a continuously rotating stepper motor.

Advantageously, the additional drive may be incorporated within the artificial valve. This facilitates implantation of the system in the patient. More preferably, the additional drive is sealed against blood ingression by being held within the rotatably displaceable valve members.

An energy source for the additional drive may advantageously be implanted in the blood vessel along with the artificial valve. More preferably, the energy source for the additional drive comprises a blood flow energy transforming device, such as an impeller, for transforming blood flow energy into electric energy.

Furthermore, the additional drive may comprise an energy storage device for temporarily storing the transformed electric energy. The energy storage device may comprise a capacitor or, in particular, a rechargeable battery. There is sufficient blood flow energy in the blood that can be used, just like a natural heart valve is driven purely by the energy of the blood flow.

The additional drive has the further advantage that a single drive can be used for continuously rotating all of the rotatably displaceable valve members.

According to a third embodiment the relative displacement of the valve members is achieved by means of braking. Accordingly, in a preferred embodiment the displacing mechanism comprises at least one brake for decelerating one or more of the rotatably displaceable valve members. Again, the braking action is appropriately controlled by a control unit.

If the artificial valve has only two rotatably displaceable valve members, a single brake for one of the two valve members would be sufficient. If the artificial valve has three or four or more rotatably displaceable valve members, two, three or more of the valve members would have to be slowed down by braking action. Accordingly, two or three or more brakes can be provided and controlled by the control unit, one for each valve member to be decelerated. However, it is preferable to use a single brake as this facilitates the controlling efforts. Such single brake could simultaneously act on all of the valve members to be decelerated. Alternatively, provided that the valve members are mechanically coupled to each other in a suitable manner, it can be sufficient to provide braking action only on one of the valve members, such as on an outermost valve member, so as to indirectly decelerate also those valve members that are mechanically coupled to the valve member on which the brake acts.

It has been described earlier in relation to the prior art that it is advantageous to provide the valve members with a plurality of blood flow passages. More specifically, the blood flow passages in each of the rotatably displaceable valve members are advantageously arranged about a common axis with an identical design pattern. It has further been described in relation to the prior art that it is advantageous to sub-divide the blood flow passages into angularly extending blood flow passage sections by means of radially extending bridges. This is important to prevent back flow through the closed valve in cases where the valve has three or more valve members arranged in series. The advantages achieved therewith are likewise advantageous for the artificial valve system of the present invention. More specifically, the bridges of each of the rotatably displaceable valve members preferably each have a center line, wherein the center lines are arranged about the common axis at an equal angular distance and the bridges each have an angular extension equal to or preferably somewhat larger than the angular extension of each of the sections of the angularly extending blood flow passages.

Unfortunately, the bridges cause turbulences in the blood flow which is generally to be avoided. In an alternative embodiment of the invention, the bridges are dispensed with. Instead, a flow restricting wall is provided so as to extend from one of the rotatably displaceable valve members through the blood flow passage of an adjacent one of the rotatably displaceable valve members to prevent transverse flow through the artificial valve when the blood flow passages of the valve members are completely out of alignment. Thus, if the artificial valve has three valve members, the flow restricting wall extends from a first one of the valve members through the blood flow passage of a second one of the valve members to the inner surface of the third valve member or through the blood flow passages of the second and third valve member. If the artificial valve has four valve members, the flow restricting wall extends through the second and third valve members to the inner surface of the fourth valve member or through the blood flow passages of the second, third and fourth valve members. This principle can likewise be applied to artificial valves having more than four rotatably displaceable valve members.

Good performance of the valve's mechanism is obtained when the valve members are made of a material inert enough to maintain over time a low friction between the surfaces forming the sealing contact. This eliminates the risk of the smooth surfaces sticking to each other. Most preferably, the valve members are made of a ceramic material. Ceramic works better than most metals, which, when mounted together with fine tolerances between surfaces, will more easily stick together over time. More particularly, with every relative sliding movement the sealing properties of ceramic sealing surface will improve over time. Preferably, the entire valve is made from ceramics. More specifically, the rotatably displaceable valve members being made of ceramics may be held in a common housing of which at least the surfaces in contact with the valve members are coated with a ceramic material.

While it is generally conceivable that the valve opens and closes according to a predetermined clock cycle, it is preferable that the control signal is influenced by external signals, such as signals depending upon the patient's momentary constitution. More particularly, the control signal may relate to a blood pressure signal. For instance, when the blood pressure on the upstream side of the valve has reached a predetermined level, a control signal causing the valve to open may be sent to the displacing mechanism.

A preferred embodiment of the valve system therefore comprises a blood pressure sensor which provides the blood pressure signal, when the system is installed in a patient. The blood pressure sensor is preferably arranged on an upstream side of the valve and may be located e.g. in a heart chamber. Most conveniently, the blood pressure sensor may be fixed to an exterior surface of the valve.

The control signal may alternatively or additionally relate to a pace maker signal. Therefore, the valve system preferably further comprises a pace maker which, when the system is installed in a patient, provides the pace maker signal to a control unit or may even directly provide the pace maker signal to a motor. In the latter case the pace maker may replace or include the control unit of the valve system.

The drive for continuously rotating the valve member is preferably an electromagnetic drive. This allows for arrangement of a stator outside the blood vessel or heart and the rotor inside the valve, the rotor being operatively connected to one or more of the displaceably arranged valve members. More specifically, the rotor of an electric motor is implanted inside the patient's blood vessel or heart along with the artificial valve so as to be driven by a locally changing electromagnetic field applied from outside the artificial valve. In this arrangement, the rotatably displaceable valve members may advantageously form an integral part of the rotor. Sine the contact between the valve members should be via ceramic material, the valve members preferably comprise magnets covered with the ceramic material.

There are a number of preferred ways for supplying the drive with energy. Preferably, an energy source provides the drive with energy from outside the blood vessel. The energy is preferably transferred wirelessly and may be consumed by the drive at the time the energy is transferred. Alternatively or in addition the energy source may comprise energy storage means, such as a battery, a capacitor, a rechargeable battery and/or any other type of accumulator. The energy storage means may be adapted to be implanted inside the patient's body either inside the blood vessel along with the artificial valve or outside the blood vessel.

Instead of a wireless energy transfer from outside the patient's body into the patient's body, the valve system may comprise galvanic coupling elements adapted to connect the energy storage means, when implanted inside the patient's body, or the drive to an extra corporal primary energy source for transmitting energy to the energy storing means or drive in contacting fashion. The extra corporal primary energy source may form a part of the overall valve system. If the energy transmission is wireless, the system may further comprise an energy transmission device for wireless energy transfer from the energy storage means to the drive and/or to the energy storage means. An implantable transforming device is provided for transforming the wirelessly transferred energy into electric energy.

The invention will now be described in more detail in context with some preferred embodiments of the invention as shown in the accompanying drawings.

DETAILED DESCRIPTION OF THE DRAWINGS

Figure 1:
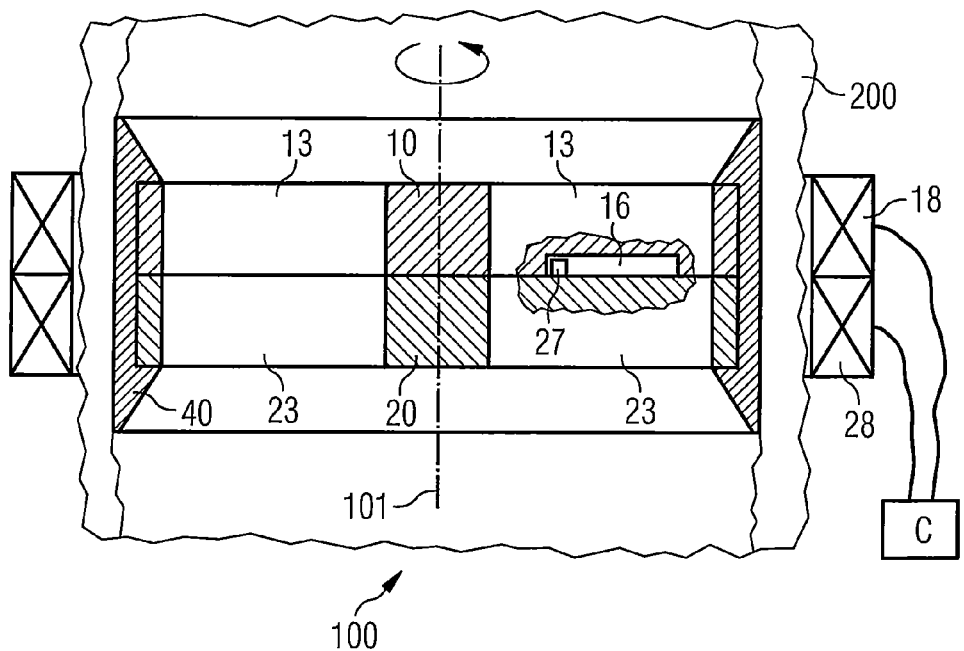
FIG. 1 shows schematically a cross sectional view of an artificial valve with two valve members according to a first embodiment.

FIG. 1 schematically shows a cross sectional view of an artificial valve or, more exactly, an artificial valve system implanted in a patient's blood vessel 200, for instance in the aorta replacing the aortic valve. The artificial valve can likewise be implanted in other blood vessels, in particular also in the heart replacing one of the internal heart valves.

The artificial valve system is generally designated with reference numeral 100 in FIG. 1. It mainly consists of three major components, the actual artificial valve inside the blood vessel 200, electromagnetic drive components 18, 28 outside the blood vessel 200 in close proximity to the artificial valve, and a control unit C controlling the electromagnetic components 18, 28. The electromagnetic components 18, 28 form stators of an electromotor, whereas the valve members 10 and 20 of the artificial valve form rotors of the electromotor cooperating with the stators. Thus, the valve members of the artificial valve form an integral part of the rotor. In order for the valve members to be driven by a locally changing electromagnetic field applied from outside the artificial valve via the electromagnetic stator components 18, 28, they comprise appropriately arranged magnets. These magnets are covered with ceramic material in order to reduce surface friction between the valve member 10 and the valve member 20 as well as between as the valve members 10, 20 and the housing 40 within which they are slidably held. Thus, upon application of a locally changing electromagnetic field applied from outside the artificial valve, the valve members 10, 20 will be caused to rotate within the housing 40, which is fixedly held in the blood vessel 200 e.g. by suturing.

Each of the valve members 10, 20 has blood flow passages 13 and 23, respectively, which extend axially through the valve members 10, 20 in parallel to the rotating axis 101. Altogether, there are four blood flow passages 13, 23 in each of the valve members 10, 20 regularly grouped about the axis 101, as can be seen in the top plan view shown in FIG. 3. In FIG. 1 the valve members 10, 20 are shown in a state of alignment of their blood flow passages 13, 23, whereas in FIGS. 2 and 3 they are shown in a state of disalignment, i.e. in a closed state of the artificial valve.

Generally the valve members 10, 20 rotate with a common regular speed imparted thereon by means of the electromagnetic stator components 18, 28, except during the time period when they change from a state of alignment to a state of disalignment, and vice versa. As can be seen from FIG. 3 (arrow), showing the artificial valve in the closed state, the valve members 10, 20 are rotating clockwise if viewed from the top. There is a pin 27 projecting from a flat surface of the lower valve member 20 into a recess 16 formed in a cooperating flat surface of the upper valve member 10. The end positions of the pin 27 in the recess 16 are chosen accurately so that the valve members 10, 20 are in an aligned (open) position when the pin 27 is at one end of the recess 16 and are in a disaligned (closed) position when the pin 27 has reached the respective other end of the recess 16.

Figure 2:
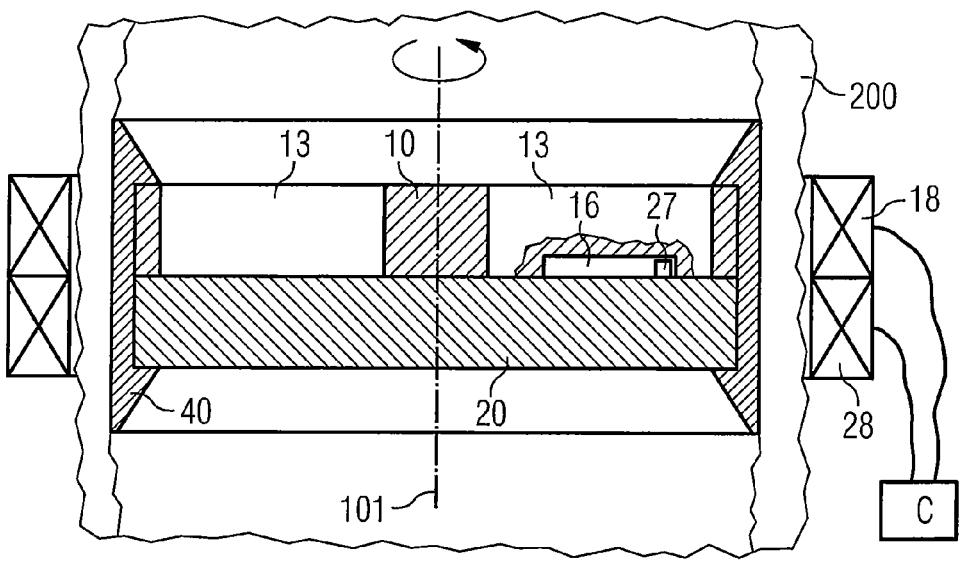
FIG. 2 shows the artificial valve of FIG. 1 in a different functional state.
Figure 3:
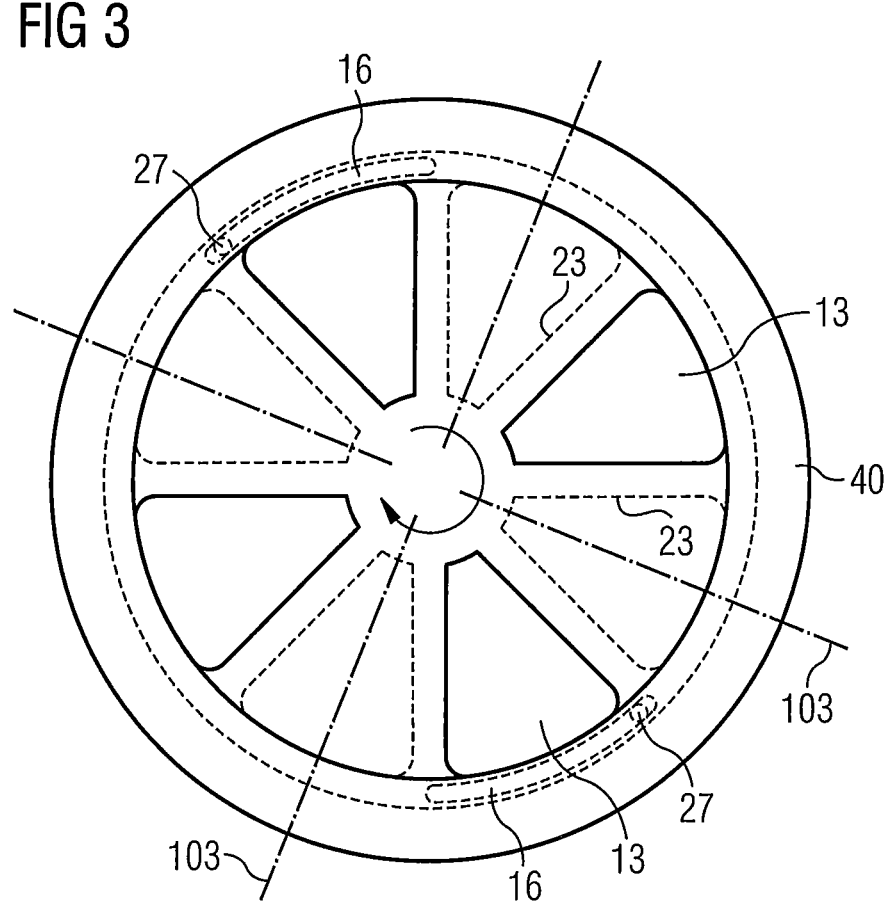
FIG. 3 shows a top plan view of the artificial valve of FIGS. 1 and 2.

In order to maintain the artificial valve in the closed position shown in FIGS. 2 and 3 and considering that the valve members 10, 20 are turning clockwise (FIG. 3), it is advantageous to apply a stronger driving force on the upper valve member 10 via the upper electromagnetic stator component 18 as compared to the force applied to the lower valve member 20 via the lower electromagnetic stator component 28, or not to apply any force to the lower valve member 20 at all. When the artificial valve is to be opened, the blood flow passages 13, 23 can be brought into alignment by accelerating the lower valve member 20 using the lower electromagnetic stator component 28. The process can be speeded up if at the same time the upper valve member 10 is somewhat slowed down or no force is applied to the upper valve member 10 at all. In the end, the same amount of driving force will be imparted on the set of valve members 10, 20, so that the regular rotating speed will not change. However, when the upper valve member 10 is not slowed down at the time of bringing into alignment the blood flow passages 13, 23, the rotational speed of the set of aligned valve members 10, 20 will slightly increase due to the increased driving force imparted by the lower electromagnetic stator component 28 on the lower valve member 20.

When the artificial valve is to be closed again from the state shown in FIG. 1 back to the state shown in FIGS. 2 and 3, this can be done in the same manner, either by increasing the rotational speed of the upper valve member 10 and at the same time decreasing the rotational speed of the lower valve member 20, or simply by decreasing the speed of the upper valve member 10 with the side effect that the rotational speed of the entire set of valve members 10, 20 will be slowed down slightly.

Figure 4:
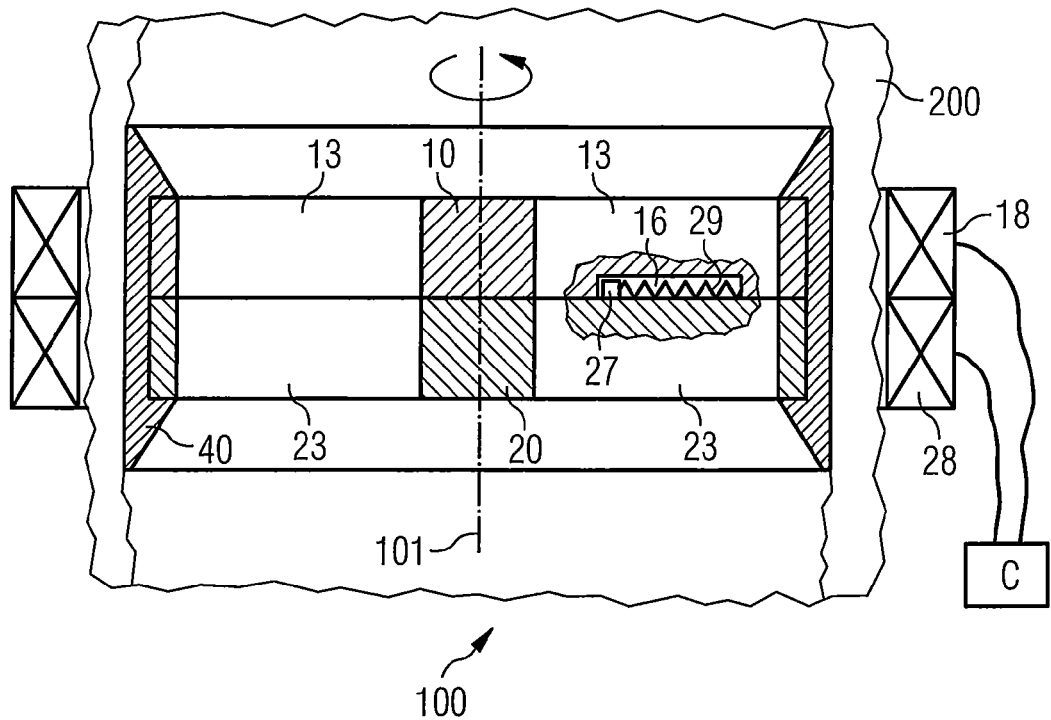
FIG. 4 shows schematically a cross sectional view of an artificial valve with two valve members according to a second embodiment.

It is preferable to maintain the artificial valve in an open state in the case that the electromagnetic drive is not active. This is important for the health of the patient in case of e.g. a power failure or other reasons. Therefore, a resilient element such as a safety spring 29 as shown in FIG. 4 is provided to urge the blood flow passages 13, 23 into at least partial alignment. The safety spring 29 acts on the pin 27 displaceably guided in the recess 16. The spring force should be as little as possible since it has to be overcome each time when the artificial valve changes from an open to a closed state (or vice versa). However, due to the valve members 10, 20 having a ceramic surface, surface friction is little so that the force of the safety spring 29 can be kept little as well.

Figure 5:
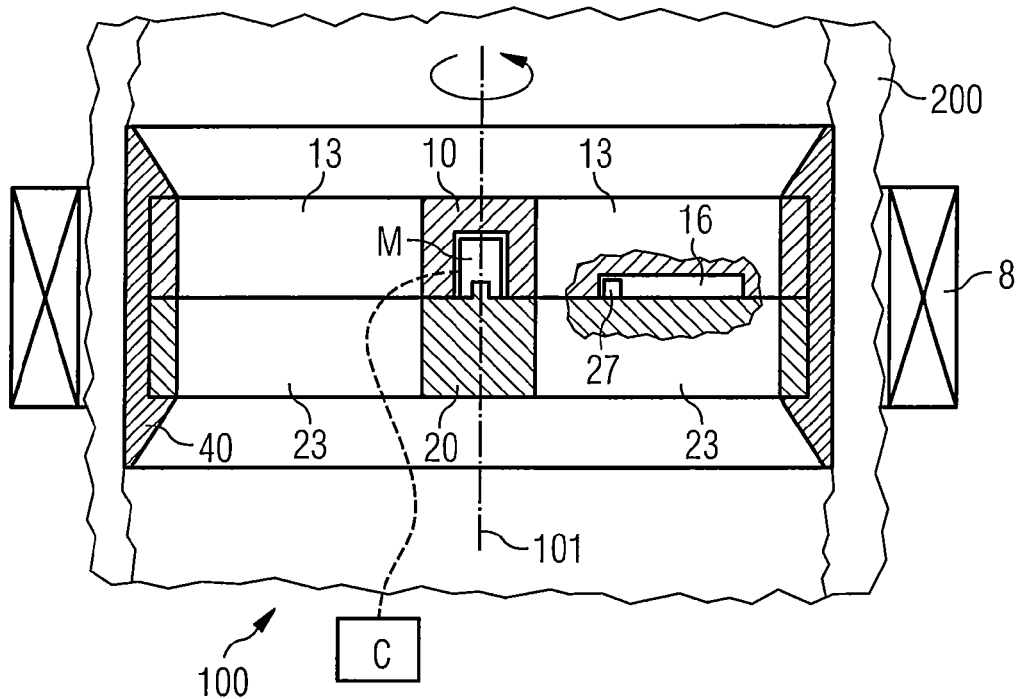
FIG. 5 shows schematically a cross sectional view of an artificial valve with two valve members according to a third embodiment.

Instead of controlling the electromagnetic stator components 18 and 28 for displacing the valve members 10, 20 relative to each other, an additional drive M may be used as shown in the embodiment according to FIG. 5. Here, a single electromagnetic stator component 8 is provided and sufficiently wide to drive the entire set of valve members 10, 20 at a regular constant rotational speed. By means of the additional drive M the relative rotational speed of the rotatably displaceable valve members 10, 20 can be temporarily changed. The additional drive M is appropriately controlled by a control C so as to bring the blood flow passages of the valve members 10, 20 into and out of at least partial alignment.

In the embodiment shown, the additional drive M mechanically interconnects the two valve members 10, 20. It is fixedly mounted, here, on the lower valve member 20 and is in driving engagement with the upper valve member 10. For instance, the additional drive M may comprise a stepper motor.

The additional drive M is incorporated within the artificial valve on the central axis 101 thereof. This way, the additional drive M is sealed against blood ingression within the rotatably displaceable valve members due to the smooth sealing surfaces of the valve members 10, 20.

Figure 6:
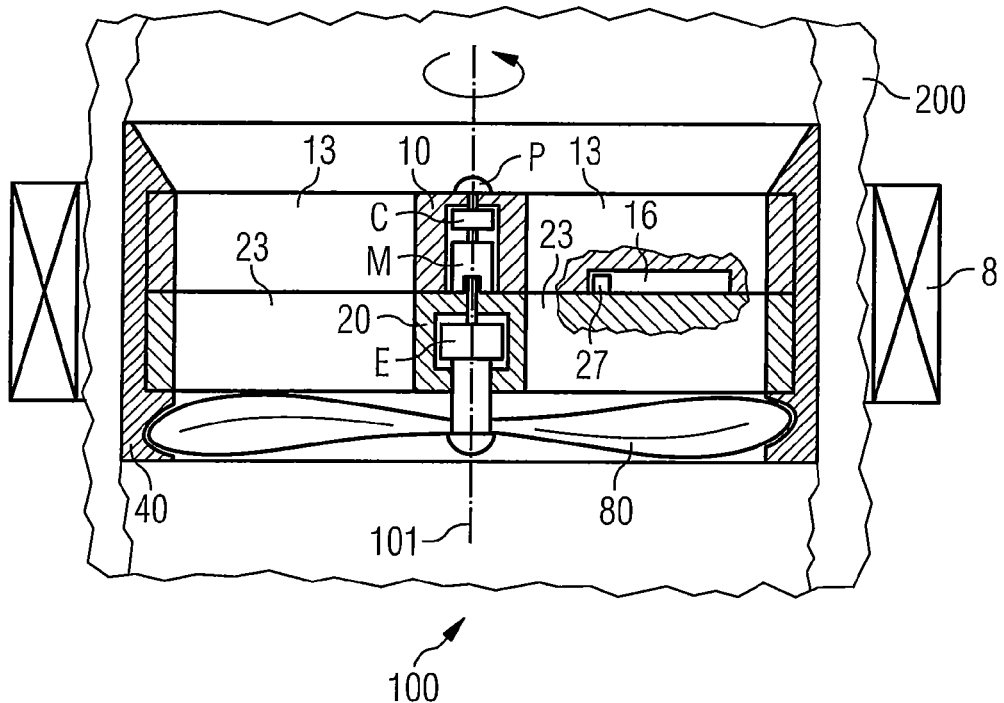
FIG. 6 shows schematically a cross sectional view of an artificial valve with two valve members according to a fourth embodiment.

While energy can be transmitted to the additional drive M either wirelessly or in contacting fashion via a sliding contact on the outer circumference of the lower valve member 20 at the interface between the lower valve member 20 and the housing 40, a preferred embodiment of providing the additional drive M with energy is shown in FIG. 6. Accordingly, the additional drive M comprises a blood flow energy transforming device 80 in the form of an impeller for transforming blood flow energy into electrical energy. The energy is temporarily stored in an energy storage device E so that it is available at the time when the control C requests the additional drive M to bring the blood flow passages 13, 23 into or out of alignment.

The control unit C is also incorporated within the artificial valve along with the additional drive M so that it is likewise sealed against blood ingression within the rotatably displaceable valve members. The energy provided by the energy transforming device 80 and stored in the energy storage device E may further be used to run the control unit C.

A blood pressure sensor B is arranged on an upstream side of the artificial valve 100 to provide an external control signal that is used by the control unit C to appropriately control the additional drive M. In other applications the blood pressure sensor can form a separate component conductively or wirelessly connected to the control unit C and may be placed e.g. in a heart chamber.

In addition to or instead of the blood pressure signal, a pacemaker signal may be used as the external control signal.

Figure 7:
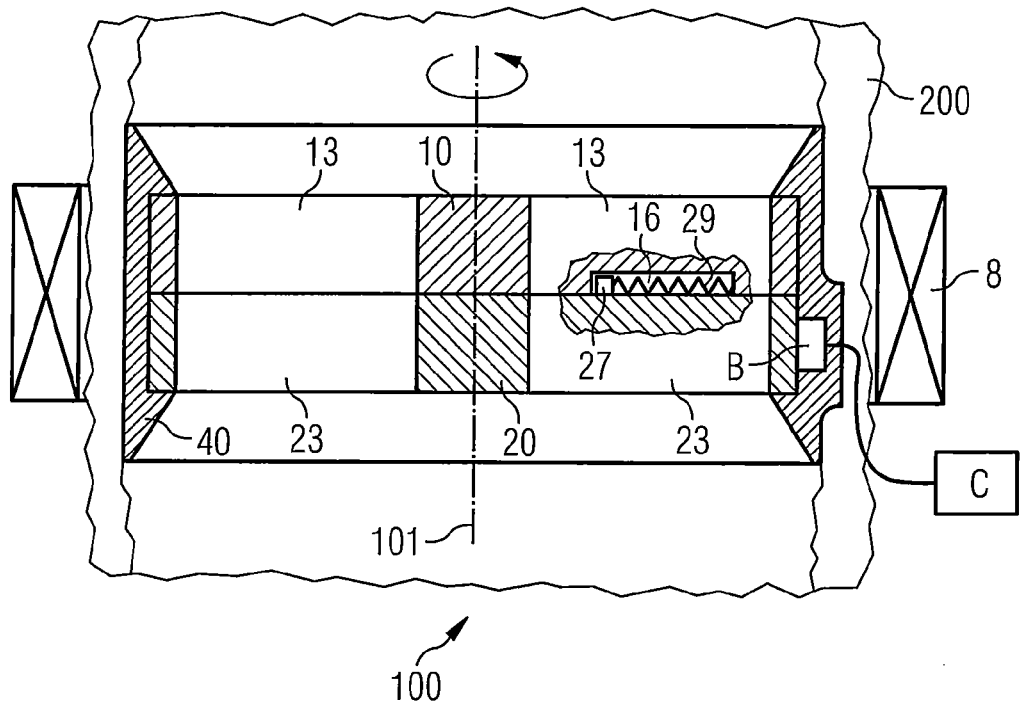
FIG. 7 shows schematically a cross sectional view of an artificial valve with two valve members according to a fifth embodiment.

A further improvement of the system will now be described in relation to FIG. 7. The embodiment shown in FIG. 7 is basically identical to the embodiment according to FIG. 4 but could likewise be identical to the other previously described embodiments. The major difference consists in a brake B. The brake B may be a mechanical brake or an electromagnetical brake counteracting the driving force of the electromagnetic stator component 8. The braking force acts on the lower valve member 20 and is controlled by a control unit C to act on the lower valve member 20 each time when the artificial valve is to be closed. That is, due to the braking action the rotational speed of the lower valve member 20 will slow down relative to the rotational speed of the upper valve member 10. As a result, the pin 27 will compress the safety spring 29 when it moves within the recess 16 of the upper valve member until it comes to a hold at the respective other end of the recess 16. Then the closed state of the artificial valve is reached as shown in FIG. 3.

Figure 8:
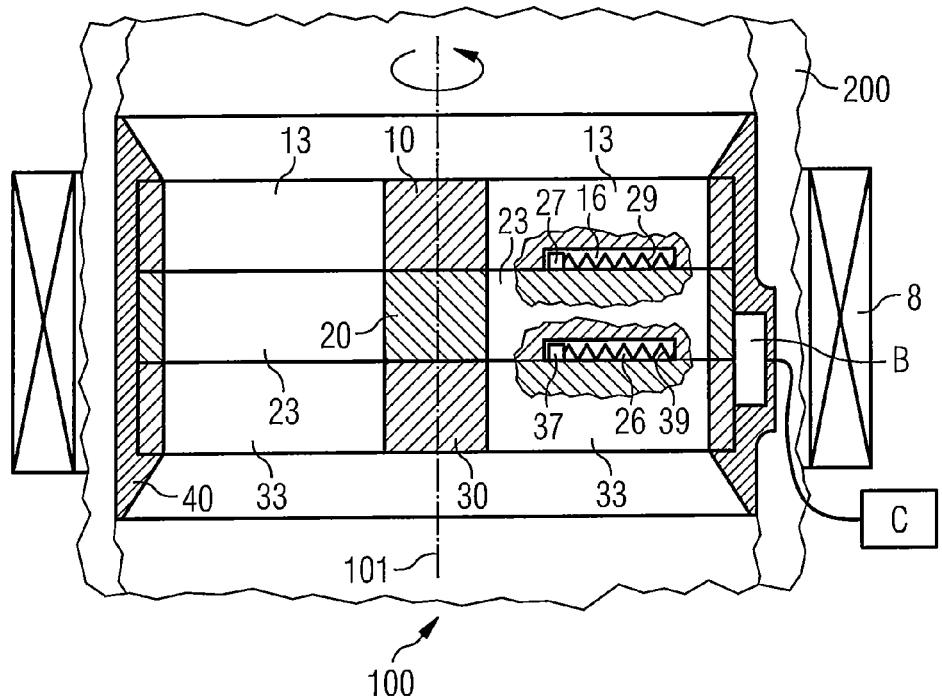
FIG. 8 shows schematically a cross sectional view of an artificial valve with three valve members according to a sixth embodiment.
Figure 18:
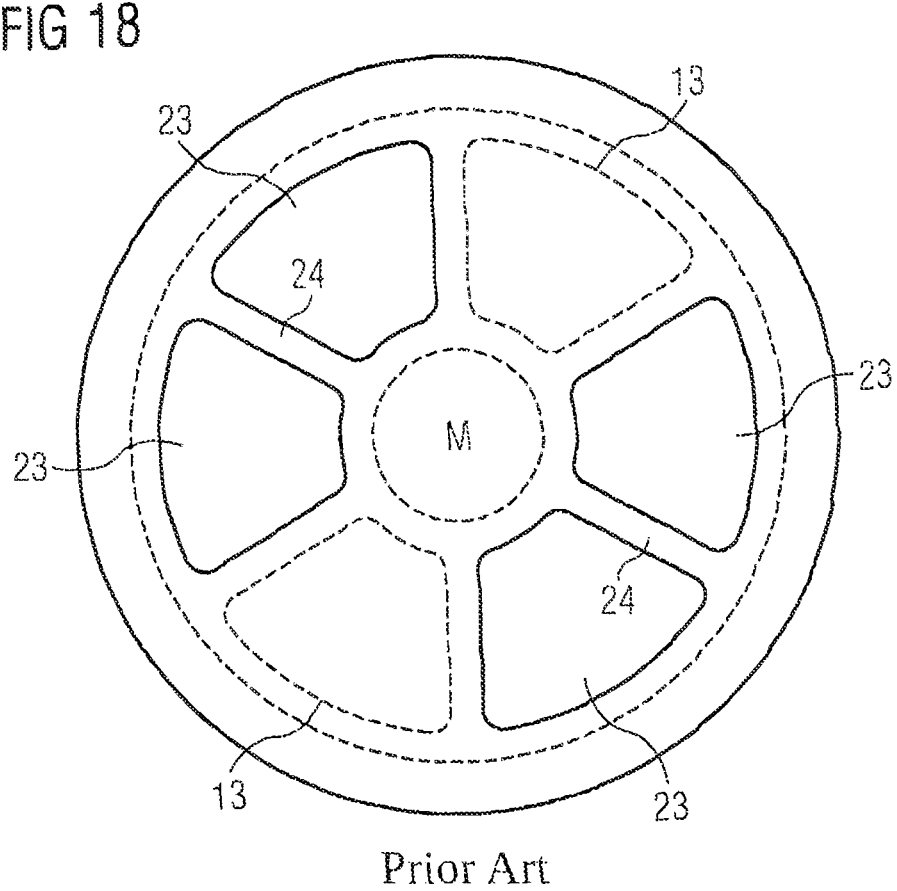

FIG. 8 shows an embodiment with three valve members 10, 20, 30 stacked one upon the other. They each have blood flow passages 13, 23, 33 that can be distributed about the central axis 101 e.g. in the same manner as shown in FIG. 18 relating to the prior art. Thus, each of the valve members 10, 20, 30 can have two blood flow passages with an angular extension of somewhat less than 120° each. The blood flow passages are subdivided in two sections via bridges 24 (FIG. 18) to prevent back flow transversely through the artificial valve when the artificial valve is in its closed position, i.e. when the blood flow passages 13, 23, 33 are in disalignment.

Each two of the valve members 10, 20 and 20, 30 are mechanically coupled by means of a pin 27, 37 extending into a recess 16, 26 so as to be movable therein between two extreme positions defining a state of aligned blood flow passages and a state of disaligned blood flow passages, respectively. Safety springs 29 and 39 acting on the pins 27, 37 are also provided in this embodiment. A brake B similar to the brake described in relation to the embodiment shown in FIG. 7 simultaneously acts on the lower two valve members 20, 30 and is controlled by a control unit C in the same manner as described before. Thus, when the brake B acts upon the lower valve members 20, 30, they will slow down quickly so as to bring the blood flow passages 13, 23, 33 out of alignment. When the braking force is released again, the lower valve members 20, 30 will assume their regular rotational speed again due to the electromagnetic driving force imparted thereon by the electromagnetic stator component 8 so that the blood flow passages 13, 23, 33 return into alignment.

Figure 9:
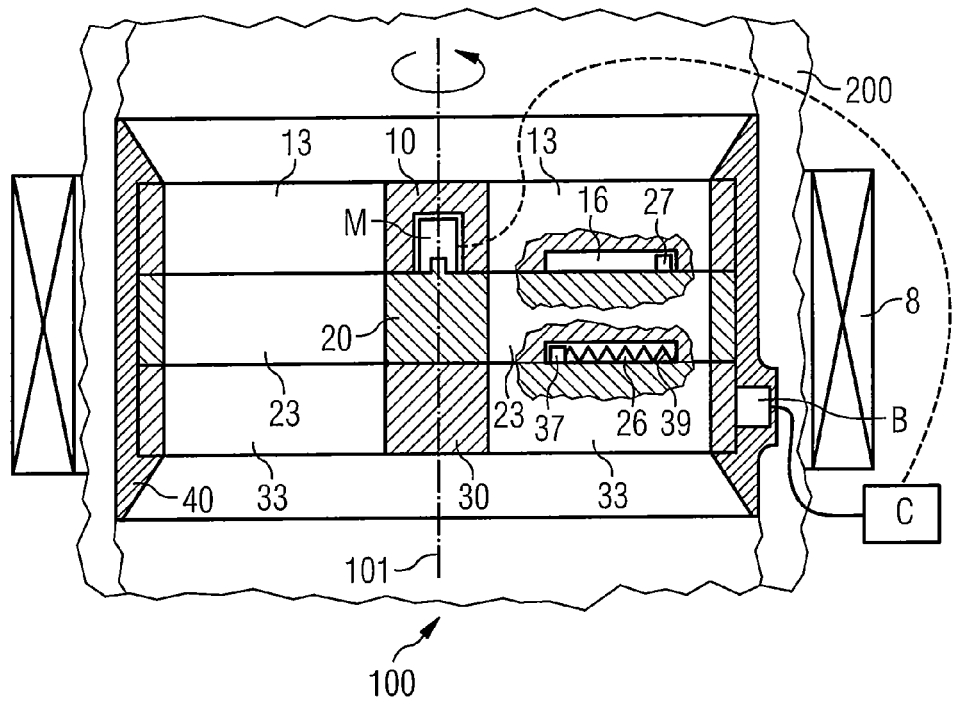
FIG. 9 shows schematically a cross sectional view of an artificial valve with three valve members according to a seventh embodiment, FIG. 10A schematically shows a top plan view of an artificial valve with four valve members according to an eighth embodiment (housing not shown)

FIG. 9 shows a variant of FIG. 8 combining features of the embodiment shown in FIG. 5 with features of the embodiments shown in FIGS. 7 and 8. That is, the upper plate 10 can be accelerated relative to the central plate 20 by means of the additional drive M mounted on the central plate 20 and in driving engagement with the upper valve member 10, whereas the lower valve member 30 can be slowed down relative to the central valve member 20 by means of the brake B acting on its outer periphery. The control unit C is galvanically coupled to the brake B and wirelessly coupled to the additional drive M, as indicated by the solid and the broken connecting lines. The pins 27, 37 moveable within the respective recesses 16, 26 will then move from their positions at one end of the recesses 16, 26, as shown in FIG. 9, to the respective other end of the recesses 16, 26 (not shown), thereby bringing the blood flow passages 13, 23, 33 out of alignment so that the artificial valve is closed (not shown).

The major difference between the embodiments shown in FIGS. 8 and 9 consists in that in the embodiment of FIG. 8 the central and lower valve members 20, 30 are slowed down whereas the upper valve member 10 is substantially maintained at the regular rotational speed. In the embodiment shown in FIG. 9, the central valve member 20 is maintained at the regular rotational speed whereas the upper valve member is accelerated in relation thereto and the lower valve member 30 is slowed down in relation thereto.

Figure 10A:
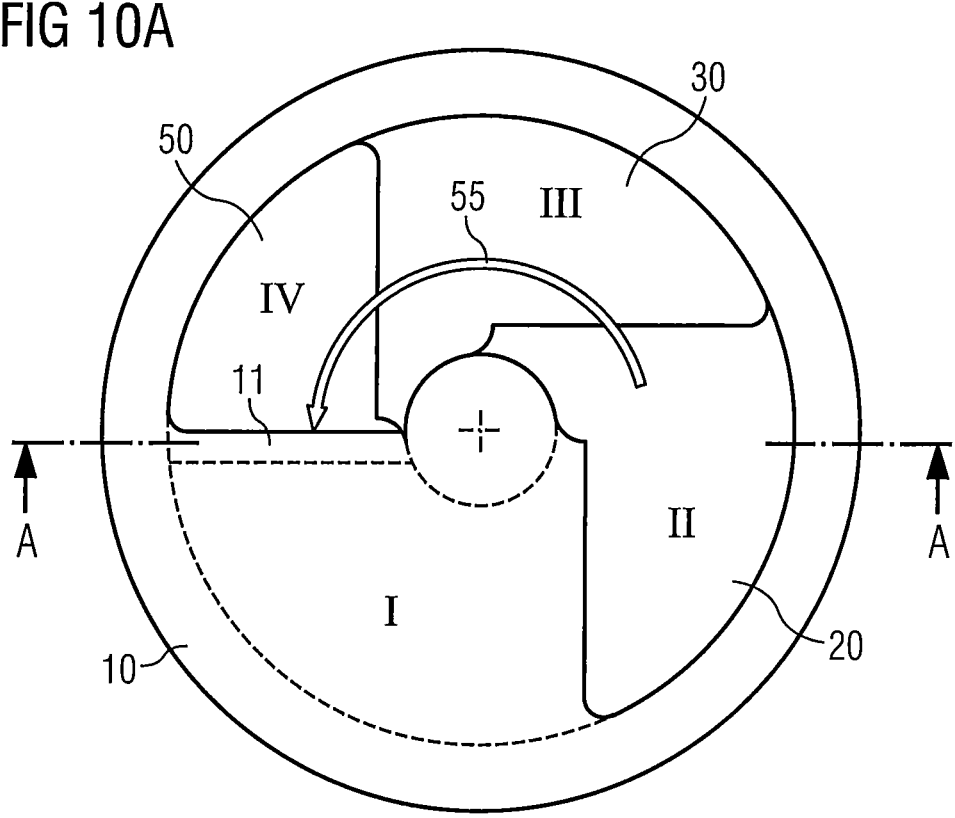
FIG. 10B shows a cross sectional view of the artificial valve of FIG. 10A (housing is shown here), FIG. 11 schematically shows the components for wireless energy and signal transfer through the patients skin, FIG. 12 schematically shows the components for conductive energy and signal transfer through the patient's skin, FIG. 13 indicates the locations for placing electromagnetic drive components outside the aorta close to the aortic valve and outside the heart close to the tricuspidalis valve.
Figure 10B:
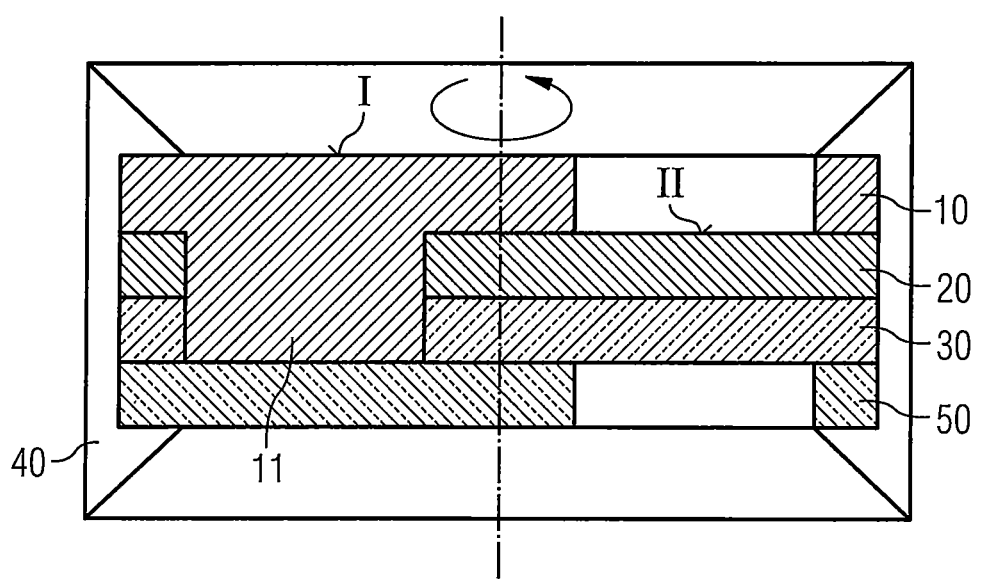

FIGS. 10A and 10B schematically show a top plan view and a cross sectional view of an artificial valve having four rotatably displaceable valve members 10, 20, 30, 50. For illustrating purposes, the housing 40 within which the valve members 10, 20, 30, 50 are slidably held is shown only in the cross sectional view according to FIG. 10B. The various embodiments described above can be realized in the artificial valve of FIGS. 10A, 10B in a similar manner. This will not be described in further detail. FIGS. 10A and 10B rather show a solution to a different problem, i.e. the problem of backflow transversely through the artificial valve when the artificial valve is in its closed position, i.e. when the valve members are so positioned that the flow path axially through the artificial valve is closed. However, in such a situation, as is indicated in FIG. 10A by arrow 55, the individual valve members form steps like in a spiral staircase so that the blood can flow from step to step transversely through the artificial valve. This problem arises when the artificial valve has more than two rotatably displaceable valve members.

In the previous embodiments shown in FIGS. 8 and 9 with three rotatably displaceable valve elements, this problem was solved with a blood flow passage configuration as shown in FIG. 18, in which the blood flow passages are symmetrically arranged about the central axis and, in addition, are subdivided into section via the bridges 24. However, the bridges 24 cause undesired turbulences. The embodiment shown in FIGS. 10A and 10B solves this problem in a different manner by means of a flow restricting wall 11 depending from the upper valve member 10 and extending through the blood flow passages of the second valve member 20 and third valve member 30 so as to reach the upper smooth surface of the lowermost rotatably displaceable valve member 50. This can be seen in the cross sectional view shown in FIG. 10B. The flow restricting wall 11 basically closes the stair case, but allows the rotatably displaceable valve members to be rotated in a clockwise manner when the blood flow passages of the valve members 10, 20, 30, 50 are to be brought into alignment so as to open the artificial valve. In the open position (not shown), the flow restricting wall 11 stops the movement of the second and third valve members 20, 30. If the flow restricting wall 11 is further extended so as to extend also through the blood flow passage of the lowermost valve member 50, it will additionally stop the movement of the lowermost valve member 50 at the time when the artificial valve is opened.

Of course, the above described principles can be applied to valves having three or more than four valve members.

Figure 11:
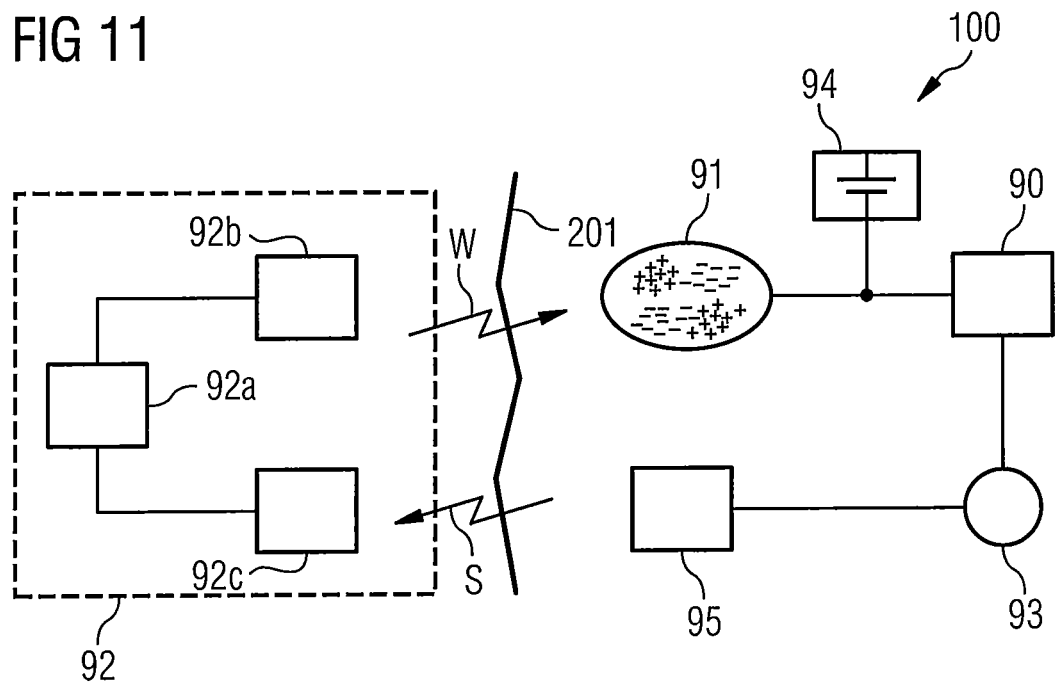

In FIG. 11, an arrangement is schematically illustrated for supplying an accurate amount of energy to an artificial valve 90 implanted in a patient, whose skin 201 is indicated by a vertical line. An artificial valve 90 is connected to an implanted energy transforming device 30, likewise located inside the patient, preferably just beneath the patient's skin 201. Generally speaking, the implanted energy transforming device 91 may be placed in the abdomen, thorax, muscle fascia (e.g. in the abdominal wall), subcutaneously, or at any other suitable location. The implanted energy transforming device 91 is adapted to receive wireless energy W transmitted from an external energy source 92a provided in an external energy transmission device 92 located outside the patient's skin 201 in the vicinity of the implanted energy transforming device 91.

As is well-known in the art, the wireless energy W may generally be transferred by means of any suitable TET-device, such as a device including a primary coil arranged in the external energy source 92a and an adjacent secondary coil arranged in the implanted energy transforming device 91. When an electric current is fed through the primary coil, energy in the form of a voltage is induced in the secondary coil which can be used to operate a valve device, e.g. after storing the incoming energy in an energy storing device or accumulator, such as a battery or a capacitor. However, the present invention is generally not limited to any particular energy transfer technique, TET-devices or energy storing devices, and any kind of wireless energy may be used.

The amount of transferred energy can be regulated by means of an external control unit 92b controlling the external energy source 92a based on a determined energy balance. In order to transfer the correct amount of energy, the energy balance and the required amount of energy can be determined by means of an internal control unit 93 connected to the artificial valve 90. The internal control unit 93 may thus be arranged to receive various measurements obtained by suitable sensors or the like, not shown, measuring certain characteristics of the artificial valve 90, somehow reflecting the required amount of energy needed for proper operation of the artificial valve 90. Moreover, the current condition of the patient may also be detected by means of suitable measuring devices or sensors, in order to provide parameters reflecting the patient's condition. Hence, such characteristics and/or parameters may be related to the current state of the artificial valve 90, such as power consumption, operational mode and temperature, as well as the patient's condition reflected by, e.g., body temperature, blood pressure, heartbeats and breathing.

Furthermore, an energy storing device or accumulator 94 may optionally be connected to the implanted energy transforming device 91 for accumulating received energy for later use by the artificial valve 90. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the artificial valve 90, and also to avoid excessive heating, it is clearly understood that the battery should be charged optimally by receiving a correct amount of energy from the implanted energy transforming device 91, i.e. not too little and too much. The accumulator may also be a capacitor with corresponding characteristics.

For example, battery characteristics may be measured on a regular basis to determine the current state of the battery, which then may be stored as state information in a suitable storage means in the internal control unit 93. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 93 is adapted to determine the energy balance and/or the currently required amount of energy (either energy per time unit or accumulated energy) based on measurements made by the above-mentioned sensors or measuring devices on the artificial valve 90, or the patient, or an energy storing device if used, or any combination thereof. The internal control unit 93 is further connected to an internal signal transmitter 95, arranged to transmit a control signal reflecting the determined required amount of energy, to an external signal receiver 92c connected to the external control unit 92b. The amount of energy transmitted from the external energy source 92a may then be regulated in response to the received control signal.

Alternatively, sensor measurements can be transmitted directly to the external control unit 92b wherein the energy balance and/or the currently required amount of energy can be determined by the external control unit 92b, thus integrating the above-described function of the internal control unit 93 in the external control unit 92b. In that case, the internal control unit 93 can be omitted and the sensor measurements are supplied directly to the internal signal transmitter 95 which sends the measurements over to the external signal receiver 92c and the external control unit 92b. The energy balance and the currently required amount of energy can then be determined by the external control unit 92b based on those sensor measurements.

Hence, the feed back of information indicating the required energy is based on the actual use of energy that is compared to the received energy, e.g. with respect to the amount of energy, the energy difference, or the energy receiving rate as compared to the energy rate used by the valve device. The artificial valve 90 may use the received energy either for consuming or for storing the energy in an energy storage device or the like. The different parameters discussed above would thus be used, if relevant and needed, as a tool for determining the actual energy balance. However, such parameters may also be needed per se for any actions taken internally to specifically operate the artificial valve 90.

The internal signal transmitter 95 and the external signal receiver 92c may be implemented as separate units using suitable signal transfer means, such as radio, IR (Infrared) or ultrasonic signals. Alternatively, the internal signal transmitter 95 and the external signal receiver 92c may be integrated in the implanted energy transforming device 91 and the external energy source 92a, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 11 may operate basically in the following manner. The energy balance is first determined by the internal control unit 93. A control signal reflecting the required amount of energy is also created by the internal control unit 93, and the control signal is transmitted from the internal signal transmitter 95 to the external signal receiver 92c. Alternatively, the energy balance can be determined by the external control unit 92b, depending on the implementation, as mentioned above. In that case, the control signal may carry measurement results from various sensors. The amount of energy emitted from the external energy source 92a can then be regulated by the external control unit 92b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 92a, such as voltage, current, amplitude, wave frequency and pulse characteristics.

Figure 12:
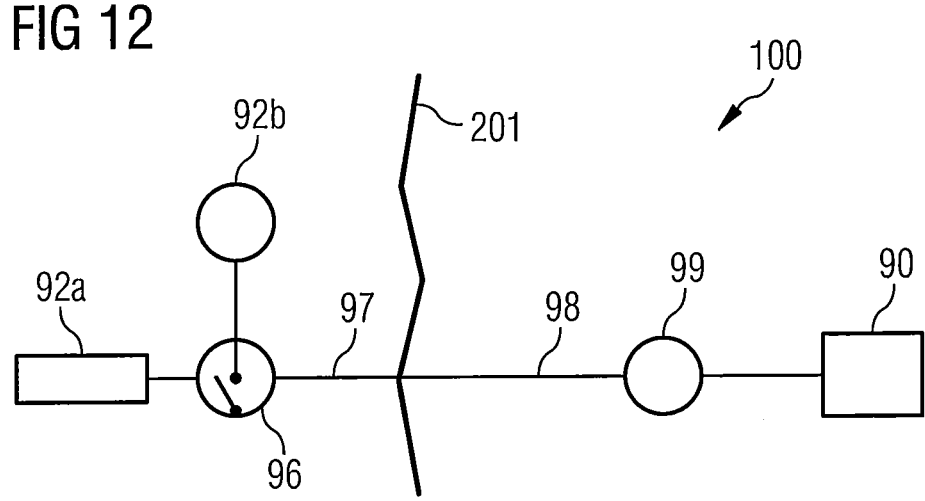

Wireless transfer of energy for operating the valve device has been described. It will be appreciated that the valve device can be operated with wire bound energy as well. One such example is shown in FIG. 12, wherein an external switch 96 is interconnected between the external energy source 92a and an operation device, such as an electric motor 99 regulating the artificial valve 90, by means of power lines 97 and 98. An external control unit 92b controls the operation of the external switch 96 to effect proper operation of the artificial valve 90.

Figure 13:
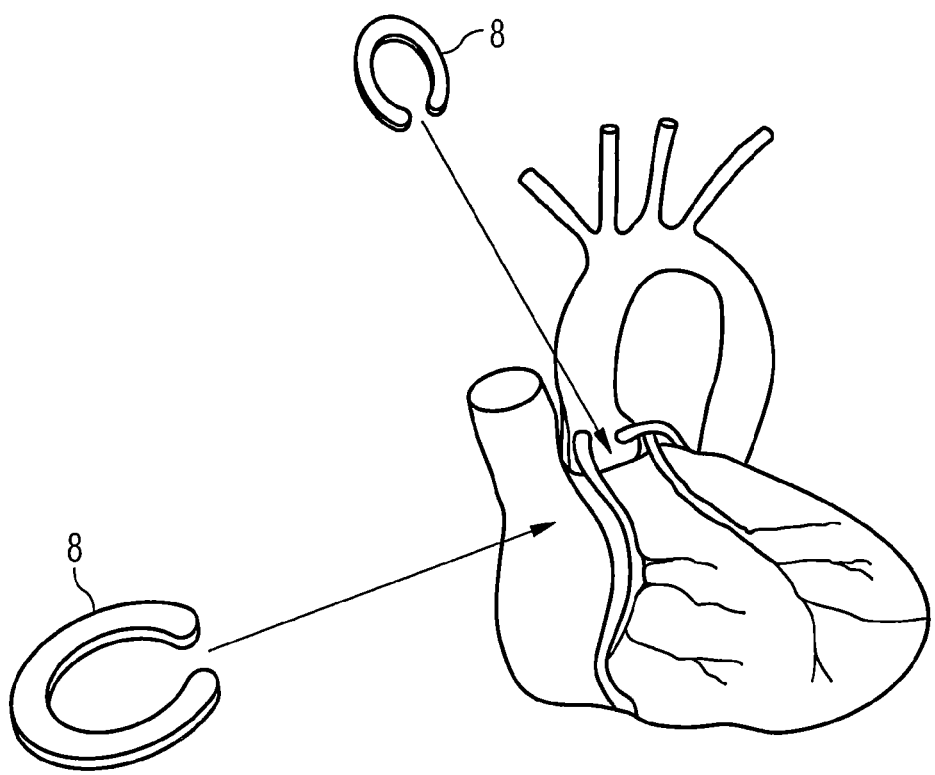
Figure 14:
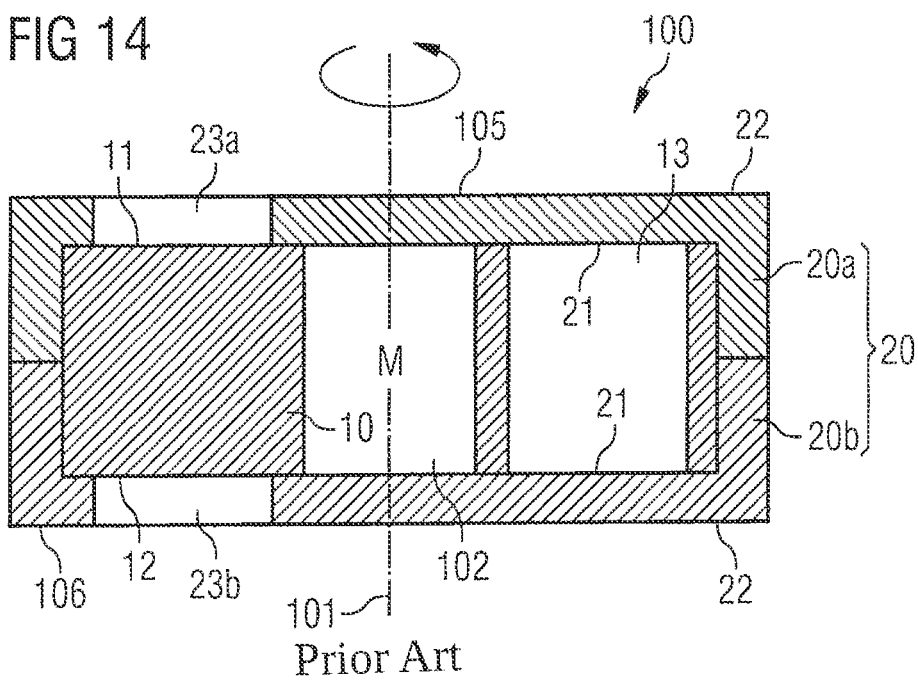
FIG. 14 shows a cross section of an embodiment of an artificial valve according to the prior art with one rotatable and one stationary valve member.
Figure 15:
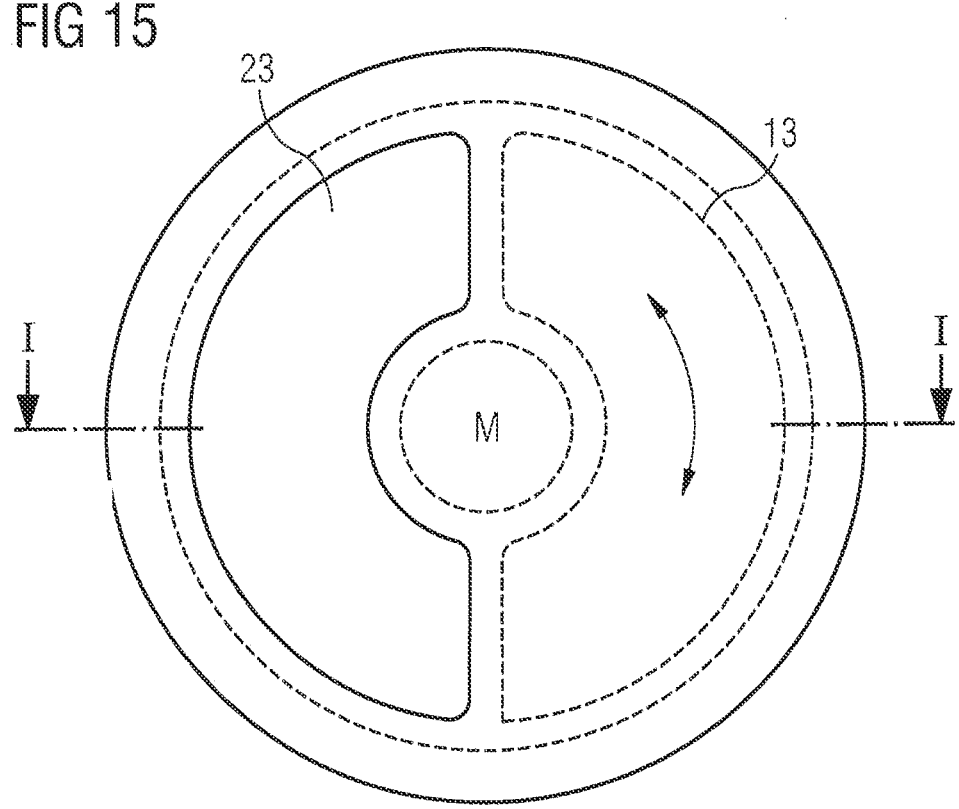
FIGS. 15 and 16 show top views of two different designs of the prior art artificial valve shown in FIG. 14 with differently arranged flow passages.
Figure 16:
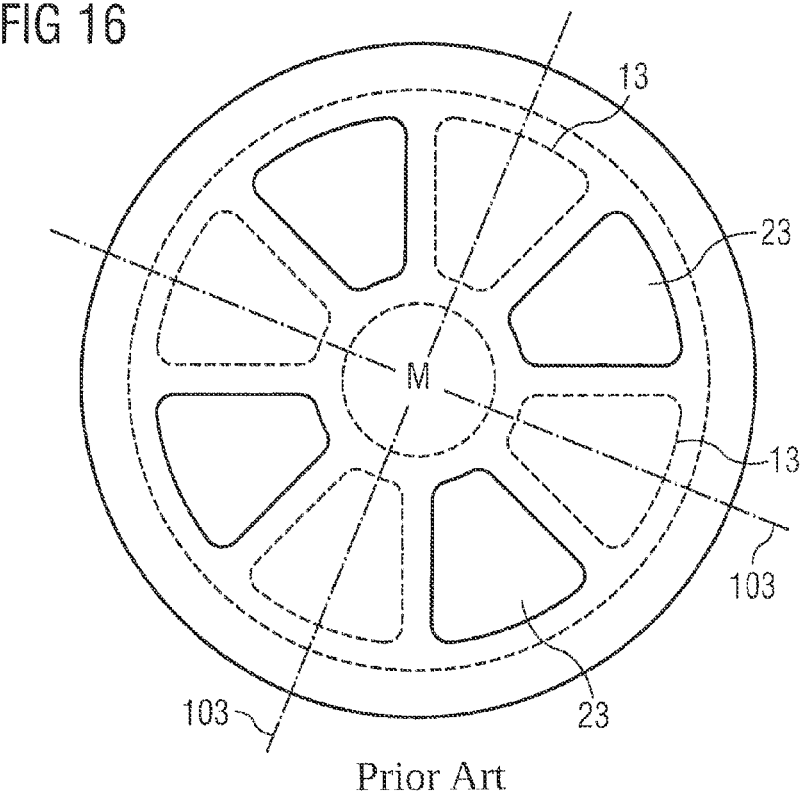
Figure 17:
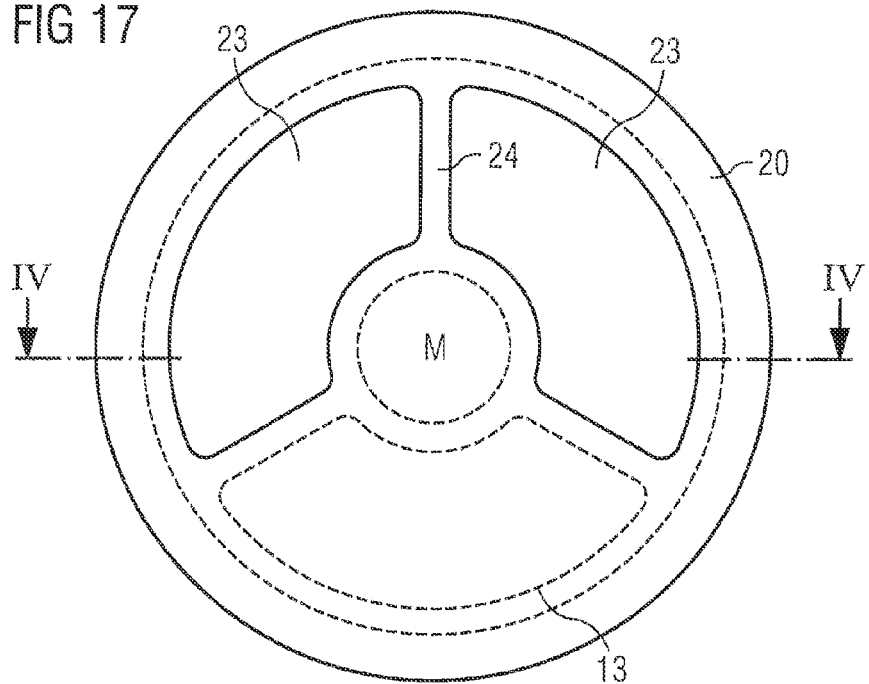
FIGS. 17 and 18 show top views of two different designs of an artificial valve according to the prior art with two rotatable and one stationary valve member and with differently arranged flow passages.

FIG. 13 generally indicates the locations where the electromagnetic stator component 8 of the artificial valve system can be placed when the artificial valve is to replace the aortic valve or the tricuspidalis valve, namely about the aorta just in front of the location where coronar blood arteries are branching off of the aorta, in the one case, and outside the heart in the area where the tricuspidalis valve separates the right ventricle from the right atrium, in the other case. The electromagnetic valve component 8 has the form of a horseshoe in the embodiment shown in FIG. 13 but can have a different form, in particular a circular form, depending upon the kind of surgery carried out on the heart or heart vessel.

The invention claimed is:

1. An artificial valve system for implantation in a patient's blood vessel, comprising
    at least a first and a second valve member each having at least one blood flow passage extending from a first surface of the respective valve member to a second surface located on an opposite side thereof, wherein at least one of the first and second valve members is arranged so as to be rotatably displaceable relative to the other of the first and second valve members such that the blood flow passages of the first and second valve members can be brought into at least partial alignment,
    at least one drive for continuously rotating the first valve member with a rotational speed and the second valve member with a rotational speed, and
    a displacing mechanism for the displacement of the first and second valve members relative to each other, the displacing mechanism being adapted to temporarily change the relative rotational speed of the first and second valve members so as to bring the blood flow passages of the first and second valve members into and out of at least partial alignment, and
    wherein the first and second valve members always rotate with the same rotational speed, unless when their relative position is to be changed to bring the blood flow passages into and out of alignment.

2. The artificial valve system of claim 1, wherein the displacing mechanism is adapted to first accelerate one of the first and second valve members and then decelerate said one valve member again in order to rotatably displace the first and second valve members relative to each other or wherein the displacing mechanism is adapted to first decelerate one of the first and second valve members and then accelerate said one valve member again in order to rotatably displace the first and second valve members relative to each other.

3. The artificial valve system of claim 1, further comprising a third valve member having at least one blood flow passage extending from a first surface of the third valve member to a second surface located on an opposite side thereof, wherein the third valve member is arranged so as to be rotatably displaceable relative to the first and second valve members such that the blood flow passage of the third valve member can be brought into at least partial alignment with the blood flow passages of the first and second valve members,
    wherein said at least one drive is adapted for continuously rotating also the third valve member with a rotational speed and
    wherein the displacing mechanism is adapted to temporarily change the rotational speed of the third valve member relative to the rotational speed of the first and second valve members so as to bring into and out of at least partial alignment the at least one blood flow passage of the third valve member with the blood flow passages of the first and second valve members.

4. The artificial valve system of claim 3, wherein, in order to rotatably displace the first, second and third valve members relative to each other, the displacing mechanism is adapted to first accelerate a first one of the first, second and third valve members and then decelerate said first one valve member again and to first decelerate a second one of the first, second and third valve members and then accelerate said second one valve member again.

5. The artificial valve system of claim 3, wherein, in order to rotatably displace the first, second and third valve members relative to each other, the displacing mechanism is adapted to first decelerate a first one of the first, second and third or valve members and then accelerate said first one valve member again and to first decelerate also a second one of the first, second and third valve members and then accelerate said second one valve member again.

6. The artificial valve system of claim 3, further comprising
    at least one further valve member having at least one blood flow passage extending from a first surface of the further valve member to a second surface located on an opposite side thereof, wherein the further so valve member is arranged so as to be rotatably displaceable relative to the other valve members such that the blood flow passage of the further valve member can be brought into at least partial alignment with the blood flow passages of the other valve members,
    wherein said at least one drive is adapted for continuously rotating also said at least one further valve member with a rotational speed and
    wherein the displacing mechanism is adapted to temporarily change the rotational speed of the further valve member relative to the rotational speed of the other valve members so as to bring into and out of at least partial alignment the at least one blood flow passage of the further valve member with the blood flow passages of the other valve members.

7. The artificial valve system of claim 6, wherein, in order to rotatably displace the first, second, third and further valve members relative to each other/ the displacing mechanism is adapted to first decelerate a first one of the first second, third and further valve members and then accelerate said first one valve member again and to first decelerate also a second one of the first/second/ third and further valve members and then accelerate said second one valve member again and together first decelerate a third one of the first, second, third and further valve members and then decelerate said third or more valve members again, wherein the displacing mechanism is adapted to begin the deceleration of the first one, second one and third one of the first, second, third and further valve members at the same moment.

8. The artificial valve system of claim 6, wherein the at least one drive is arranged to drive at least one of the first, second, third and further valve members with a constant rotational speed, this speed being substantially maintained during the acceleration or deceleration of other valve members.

9. The artificial valve system of claim 1, comprising a stopper arranged to hold one of said valve members in a stable position relative to a respective other one of said valve members when the blood flow passages of the valve members have reached a position of at least partial alignment, or when the blood flow passages of the valve members have reached a position of disalignment, or both when the blood flow passages of the valve members have reached a position of at least partial alignment and when the blood flow passages of the valve members have reached a position of disalignment.

10. The artificial valve system of claim 1, wherein means are provided to urge the blood flow passages into at least partial alignment when the displacing mechanism is not activated.

11. The artificial valve system of claim 1, wherein a separate drive is provided for each of at least two of the rotatably displaceable valve members and wherein the displacing mechanism comprises a control for controlling the separate drives differently so as to bring the blood flow passages of said at least two rotatably displaceable valve members into and out of at least partial alignment.

12. The artificial valve system of any of claim 1, wherein the displacing mechanism comprises an additional drive (M) for temporarily changing the relative rotational speed of at least two of the rotatably displaceable valve members and wherein the displacing mechanism further comprises a control for controlling the additional drive so as to bring the blood flow passages of said at least two rotatably displaceable valve members into and out of at least partial alignment.

13. The artificial valve system of claim 12, wherein the additional drive mechanically interconnects said at least two rotatably displaceable valve members.

14. The artificial valve system of claim 13, wherein the additional drive comprises a stepper motor.

15. The artificial valve system of any of claim 12, wherein the additional drive at least partly is incorporated within the rotatably displaced valve members.

16. The artificial valve system of claim 12, wherein the additional drive is provided with an energy source adapted to be implanted along with the artificial valve, wherein the energy source for the additional drive comprises a blood flow energy transforming device for transforming blood flow energy into electrical energy and a capacitor for temporarily storing the transformed electrical energy, when implanted.

17. The artificial valve system of claim 1, comprising an energy source which comprises an energy storage, comprising at least one of a battery, a capacitor, a rechargeable battery and any other type of accumulator, wherein the energy is adapted to be implanted inside the patient's body either inside the blood vessel along with the artificial valve or outside the blood vessel for supplying energy to the artificial valve system.

18. The artificial valve system of claim 1, wherein surfaces of the valve members forming a sealing contact comprise a ceramic material.

19. The artificial valve system of claim 1, wherein the displacing mechanism comprises at least one brake for decelerating one or more of the rotatably displaceable valve members and wherein the displacing mechanism further comprises a control for controlling the at least one brake.

20. The artificial valve system of claim 1, wherein the displacing mechanism is influenced by external control signals.

21. The artificial valve system of claim 20, further comprising a pacemaker, adapted to, when the system is installed on a patient, provide a pacemaker signal relating to the control signal or directly providing the control signal according.

22. The artificial valve system of claim 1, wherein the at least one drive comprises a rotor of an electric motor, said rotor being adapted to be implanted inside a patient's blood vessel along with the artifcial valve and to be driven by a locally changing electromagnetic field applied from outside the artificial valve, outside the blood vessel.

23. The artificial valve system of claim 1, further comprising an implanted energy transmission device for wireless energy transfer from the implanted energy source to the drive.

24. The artificial valve system of claim 23, wherein the drive is adapted to directly transform wireless transferred energy into kinetic energy.

25. The artificial valve system of any of claims 1, further comprising an external energy transmission device for wireless energy transfer from outside the patient's body to at least one of; the drive for use by the drive at the time the energy is transferred, and an implanted energy source being an energy storage adapted to be implanted inside the patient's body.

* * * * *